(12) United States Patent
Potyrailo et al.

(10) Patent No.: US 10,989,709 B2
(45) Date of Patent: Apr. 27, 2021

(54) METHODS AND SYSTEMS FOR DETECTION OF TARGET AND APPLICATIONS THEREOF

(71) Applicant: CYTIVA SWEDEN AB, Uppsala (SE)

(72) Inventors: Radislav Alexandrovich Potyrailo, Niskayuna, NY (US); Andrew David Pris, Altamont, NY (US); Nandini Nagraj, Clifton Park, NY (US); Anthony John Murray, Lebanon, NJ (US)

(73) Assignee: CYTIVA SWEDEN AB, Uppsala (SE)

( * ) Notice: Subject to any disclaimer, the term of this patent is extended or adjusted under 35 U.S.C. 154(b) by 235 days.

(21) Appl. No.: 15/465,970

(22) Filed: Mar. 22, 2017

(65) Prior Publication Data

US 2017/0191992 A1    Jul. 6, 2017

Related U.S. Application Data

(62) Division of application No. 14/043,895, filed on Oct. 2, 2013, now abandoned.

(51) Int. Cl.
*G01N 33/53* (2006.01)
*G01N 33/543* (2006.01)

(52) U.S. Cl.
CPC ..... *G01N 33/5306* (2013.01); *G01N 33/5308* (2013.01); *G01N 33/54306* (2013.01); *G01N 33/54386* (2013.01)

(58) Field of Classification Search
None
See application file for complete search history.

(56) References Cited

U.S. PATENT DOCUMENTS

| | | | | |
|---|---|---|---|---|
| 5,624,537 A * | 4/1997 | Turner | ................... | C12Q 1/002 204/402 |
| 5,683,916 A | 11/1997 | Goffe et al. | | |
| 5,998,588 A * | 12/1999 | Hoffman | ................... | B82Y 5/00 424/178.1 |
| 6,258,275 B1 | 7/2001 | Freitag et al. | | |
| 6,426,086 B1 | 7/2002 | Papahadjopoulos et al. | | |
| 6,867,268 B2 | 3/2005 | Vaidya et al. | | |
| 7,157,603 B2 | 1/2007 | Hilbrig | | |
| 7,371,852 B2 | 5/2008 | Hardeman et al. | | |
| 2008/0293926 A1 | 11/2008 | Hallgren et al. | | |
| 2010/0055068 A1 | 3/2010 | Santerre et al. | | |
| 2010/0151465 A1 | 6/2010 | Ju et al. | | |
| 2011/0070574 A1 * | 3/2011 | Borg | ................... | G01N 21/553 435/5 |
| 2011/0190483 A1 | 8/2011 | Jayawickramarajah | | |
| 2012/0010390 A1 | 1/2012 | Van Alstine et al. | | |

OTHER PUBLICATIONS

Majd et al., "The Affinity Precipitation for the Isolation of Biomolecules", Thesis, Ecole Polytechnique Federale de Lausanne, pp. 1-146, 2007.
Ashok Kumar et al., "Smart Polymers: Physical Forms and Bioengineering Applications", Available online at www.sciencedirect.com, Received Feb. 22, 2007, received in revised form May 22, 2007, accepted May 22, 2007, Prog. Polym. Sci. 32 (2007) 1205-1237.
Ashwani K. Sharma et al., "Small-Molecule-Dependent Split Aptamer Ligation", Department of Chemistry and the Center for Cell and Genome Science, University of Utah, Salt Lake City, Utah 84112, United States, Journal of the American Chemical Society, 4 Pages.
Eric Stern et al., "Label-free biomarker detection from whole blood", Advance online Publication, www.nature.com, naturenanotechnology, 5 Pages.
Lindsay Arnold et al., "Novel thermo-responsive fucose binding ligands for glycoprotein purification by affinity precipitation", 19 Pages.

\* cited by examiner

*Primary Examiner* — Andrea S Grossman
(74) *Attorney, Agent, or Firm* — Jeff B. Vockrodt; Culhane Meadow, PLLC

(57) ABSTRACT

A method of recovering a target from a sample is provided. The method of recovering the target follows different steps. The steps include providing a binding element, wherein the binding elements are immobilized on a solid support, adding the sample comprising the target to the binding element to form a binding element-target complex; washing the binding element-target complex; and eluting the target from the binding element-target complex. The system for reversible detection of target in a range from 2 to 1,000,000 bind/release cycles is also provided.

12 Claims, 8 Drawing Sheets

METHODS AND SYSTEMS FOR DETECTION OF TARGET AND APPLICATIONS THEREOF

CROSS REFERENCE TO RELATED APPLICATIONS

This application is a division of U.S. patent application Ser. No. 14/043,895, filed Oct. 2, 2013, now copending, the entire disclosure of which is incorporated herein by reference.

STATEMENT REGARDING FEDERALLY SPONSORED RESEARCH & DEVELOPMENT

This invention was made with Government support under contract number HSHQDC-10-C-00206 awarded by the Department of Homeland Security. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 30, 2013, is named 272208-1_SL.txt and is 730 bytes in size.

FIELD OF INVENTION

The invention generally relates to methods and systems for target detection using nucleic acid based binding elements capable of undergoing repeated regeneration cycles.

BACKGROUND

Binding elements including affinity ligands, such as antibodies are valued for their high selectivity and affinity, however, the stability of the molecules for their size and complex structure is an issue. Engineered protein binders have proved to be successful as affinity ligands for their small size, stability, and ease of synthesis in microbial production systems, however these binders might be unsuitable for therapeutic applications because of their potential immunogenicity. Additionally, the protein binders are expensive, and are not suitable for repeated use. Alternate binding elements based on nucleic acids, such as DNA or RNA have been developed for target specific binding.

Binding elements that offer higher stability, selectivity and specificity towards the target and provide solutions to fit both the single-use and multiple-use paradigms are highly desirable. Moreover, reusability of the binding elements for detection of multiple targets is a current need, which may reduce the expense of the detection process.

BRIEF DESCRIPTION

In one embodiment, a method of recovering a target from a sample, comprises providing a substrate coupled binding element, wherein the binding element is immobilized on a solid support; adding the sample comprising the target to the substrate coupled binding element to form a substrate coupled binding element-target complex; washing the substrate coupled binding element-target complex; and eluting the target from the substrate coupled binding element-target complex.

In another embodiment, a method for reversible detection of a target, comprises immobilizing one or more binding elements on a sensor surface, contacting a sample comprising an unknown concentration of the target to the binding elements on the sensor surface to form a binding element-target complex in a target binding event; detecting the target-binding event with a detector to generate a detection signal; eluting the target from the binding element-target complex in an elution event; applying a regeneration solution to complete the removal of the target bound to the binding element in a regeneration event; determining a number of the target-binding event, the elution event, regeneration event or combinations thereof; and applying a correction to the detection signal based on the number of the binding event, the elution event, the regeneration event or combinations thereof during the reversible detection of the target over at least 100 bind/release cycles.

In another embodiment, a method for reversible detection of a target and quantitation of a target concentration in a sample, comprises immobilizing one or more binding elements on a sensor surface, contacting a sample comprising the target to the binding elements to form a binding element-target complex in a target binding event; detecting the target-binding event with a detector to generate a detection signal; eluting the target from the binding element-target complex in an elution event; applying a regeneration solution to regenerate the binding element in a regeneration event; determining a number of the target binding event, the elution event, the regeneration event or combinations thereof; and applying a correction to the detection signal based on the number of the target binding event, the elution event, the regeneration event or combinations thereof during the reversible detection of the target and quantitation of the target concentration over at least 100 bind/release cycles.

In one embodiment of a system for reversible detection of a target, the system comprises a sample holder comprising one or more binding elements immobilized on a surface, wherein the surface is configured to load a sample comprising the target to complete a binding event forming a binding element-target complex; an inlet to supply at least a first solution to wash the binding element-target complex; an inlet to supply at least a second solution to elute the target from the binding element-target complex to complete an elution event; a detector to generate a detection signal in proportion to the concentration of the target in the sample; and a processor for calibrating performance of the system for reversible operation of the immobilized binding elements.

In another embodiment, a system for reversible detection of a target, comprises a sample holder comprising one or more binding elements immobilized on a surface of the sample holder, wherein the surface is configured to load a sample comprising the target to form a binding element-target complex to complete a binding event; an inlet to supply at least a first solution to wash the binding element-target complex to complete a washing event; an inlet to supply at least a second solution to elute the target from the binding element-target complex to complete an elution event; a target-concentration detector to generate a detection signal in proportion to a concentration of the target in the sample; a counter for counting the binding event, washing event, elution event or combinations thereof; and a processor for calibrating a performance of the system based on a number of prior performed bind-release cycles for accurate reversible operation of the immobilized binding elements.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
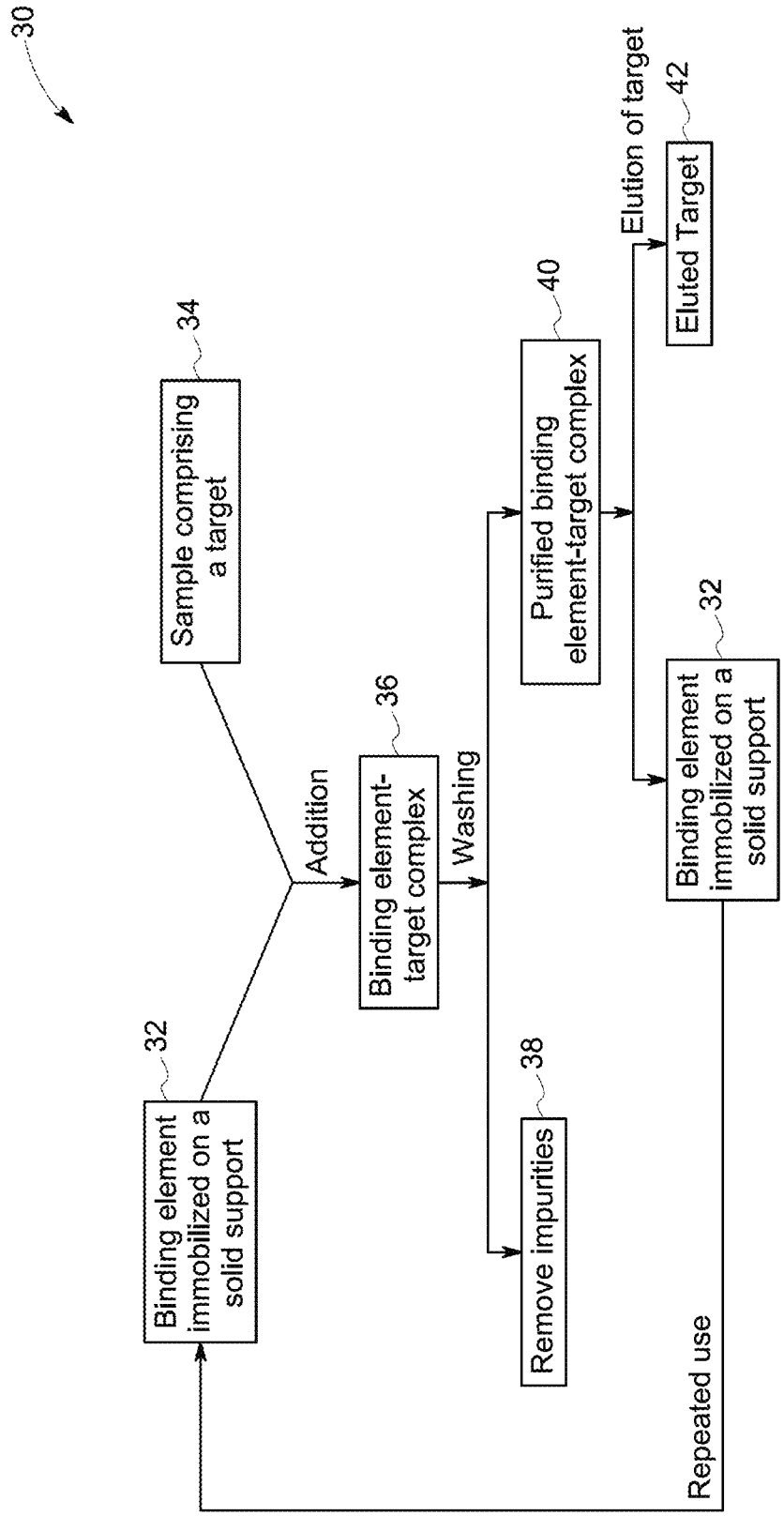
FIG. 1 is a flow chart showing a method for target detection using binding elements in accordance with one embodiment of the invention.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein, the term "bind/release cycle" refers to the sequence of events that include introducing a sample comprising a target to a surface comprising binding elements immobilized onto the surface, such as a sensor surface, binding the target to the binding element to form a binding element target complex, applying a washing solution to the a binding element target complex, applying an elution and/or applying a regeneration solution to the binding element target complex to elute the target and regenerate the binding element for subsequent use. The term "bind/release cycle" or "cycles" are interchangeably used hereinafter.

As used herein the term "nucleotide" or "nucleotide base" refers to a nucleoside phosphate. The term includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleotide triphosphate (dNTP) or a nucleotide triphosphate (NTP). The nucleotides may be represented using alphabetical letters, for example, A denotes adenosine (e.g., a nucleotide containing the nucleobase, adenine), C denotes cytosine, G denotes guanosine, and T denotes thymidine.

As used herein, the term "oligonucleotide" refers to oligomers of nucleotides or derivatives thereof. The term "nucleic acid" as used herein refers to polymers of nucleotides or derivatives thereof. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right. The oligonucleotides/nucleic acids may be a DNA, an RNA, or their analogues (e.g., uracil, inosine analogue). The oligonucleotides or nucleic acids may also include modified bases and/or backbones (e.g., modified phosphate linkage such as thiophosphate or modified sugar moiety, such as locked nucleic acid). Non-limiting examples of synthetic backbones that confer stability and/or other advantages to the nucleic acids may include phosphorothioate linkages, peptide nucleic acid, locked nucleic acid, xylose nucleic acid, or analogues thereof. The oligonucleotide refers to a linear oligonucleotide that may include 5 to 1000 nucleotides. Both the upper and lower limits of the length of the oligonucleotide are empirically determined. The lower limit on oligonucleotide length is the minimum length that is required to form a transient complex upon binding with the target molecule under desired reaction conditions. Very short oligonucleotides (usually less than 3-4 nucleotides long) do not form thermodynamically stable complex with target molecule under such conditions. The upper limit of oligonucleotide length is the maximum length that the linear oligonucleotide sequence can be accurately amplified (usually around 1000-5000 nucleotides).

The oligonucleotides may also be interchangeably referred to herein as "oligomers" or "short oligomers". The oligonucleotide may be an RNA sequence, a DNA sequence, or a chimeric sequence comprising different bases. The oligonucleotide may contain natural, synthetic, or modified nucleotides. Generally, suitable oligonucleotide lengths are in the range of 4-5000 nucleotides, more specifically, between 4-100 nucleotides long.

In some embodiments, the oligonucleotide refers to a linear oligonucleotide that may include 5 to 1000 nucleotides. The upper limit of oligonucleotide length may be the maximum length that the linear oligonucleotide sequence be accurately amplified (usually around 1000-5000 nucleotides). Suitable oligonucleotide lengths may be in the range of 4-5000 nucleotides, or between 4-100 nucleotides long.

As used herein, the term "target molecule" refers to a molecule that is of interest to determine its concentration in the analyzed sample. The target molecule may be an organic molecule, an inorganic molecule, a biological molecule, a synthetic molecule or combinations thereof. In one or more embodiments, the target molecule may be a protein, a post-translationally modified protein, a peptide, a carbohydrate, a drug, a carrier, a small molecule, an adapter, an epitope or combinations thereof. The target molecule may comprise a single entity or a multiple entity. In one example, a cell-surface protein is a single entity, which has only one binding motif and that can be a single entity target.

As noted, the target molecule may comprise a multiple entity, such as, one or more cell-surface proteins have epitopes that are associated with multiple single entities. For example, the target may be a specific combination of epitopes, such as, a multi-subunit protein complex or a section of a cell surface comprising the multi-subunit protein. In another example, when the target molecule comprises a multiple entity, the non-limiting examples of a multiple entity include surface of a cell, surface of a virus, surface of a tissue, at least two outer regions of a folded polymer molecule, at least two outer regions of a folded biopolymer molecule, a surface of an inorganic amorphous material, and a surface of an inorganic crystalline material. In these examples the binding element for such a target has a single binding motif or more than one binding motif.

The term "binding element" refers to herein as an oligonucleotide-based component that efficiently binds to a target molecule through one or more binding sites through different types of interactions, including but are not limited to, hydrophobic, Van der Waals interactions and hydrogen bonding. The binding element may include an aptamer, such as deoxyribonucleic acid (DNA) aptamer, ribonucleic acid (RNA) aptamer or peptide nucleic acid (PNA) aptamer.

One or more embodiments of the invention are directed to methods for detection and recovery of a target from a sample using binding elements. In one embodiment, a method of recovering a target from a sample, comprises providing a substrate coupled binding element, wherein the binding element is immobilized on a solid support; adding the sample comprising the target to the substrate coupled binding element to form a substrate coupled binding element-target complex; washing the substrate coupled binding element-target complex; and eluting the target from the substrate coupled binding element-target complex. The terms "substrate coupled binding element-target complex" and "complex" are interchangeably used hereinafter."

The target molecule and the binding element are in contact, which enable the binding elements to bind to the target molecules and form a substrate coupled binding element-target complex. In some embodiments, the target molecule and the binding element are mixed thoroughly to form a binding element-target complex in a first solution. In one or more embodiments, the target molecules and the binding elements are mixed in the first solution using different mixing techniques, such as by pipetting up and down, vortexing, mild shaking, waving or stirring. In one or more embodiments the target molecules and the binding element are incubated at a specific temperature without any mixing or agitation.

As noted, the method comprises addition of the sample to the binding element, wherein the target and the binding element may be in contact to each other, which results in formation of a substrate coupled binding element-target complex. In some embodiments, the plurality of binding elements has affinity for the target molecules. As noted, the method comprises forming a binding element-target complex. The term "binding element-target complex" refers to a complex wherein a binding element is bound to a target molecule. In some embodiments, the addition of substrate coupled binding element to the target forms a substrate coupled binding element-target complex. The term "binding element-target complex" or "complex" is interchangeably used hereinafter. In these embodiments, the first solution comprises the substrate coupled binding element-target complex, excess unbound target, other molecules and impurities. As mentioned, the "other molecules", these molecules may have structural similarity with the target.

The affinity of the binding element for the target molecules may enhance the binding efficiency of the binding element to the target. In some embodiments, the binding elements are bound to the target molecules by ionic interaction, H-bonding, Vander Waal's forces or combinations thereof. In some embodiments, the binding element target complex is stabilized by adding a reaction buffer to the mixture. In one embodiment, the binding element-target complex comprises the binding element and the target in 1:1 ratio.

In one or more embodiments, as noted, the binding element is immobilized on a solid support. In one or more embodiments, the method comprises providing a binding element immobilized on a solid support, adding a sample comprising a target to the substrate coupled binding element to form a binding element-target complex that is immobilized to the solid support. The binding element-target complex is washed followed by elution of the target from the binding element-target complex. In one or more embodiments of the method, the binding element immobilized on a solid support is recycled for multiple times.

The binding element immobilized on a solid support may be recycled for 2 to 100,000 times, in some other embodiments, the binding element immobilized on a solid support is recycled for 2 to 100 times. The structural integrity of the substrate coupled binding element remains intact, which ensures binding efficiency of the binding element to the target for multiple cycles. As noted earlier, the term, "bind/release cycle" or "cycles" are used herein interchangeably to describe a complete event that is combination of the binding event, washing event, the elution event and regeneration event. In case of multiple cycles, for example, a target binds to the binding element and followed by elution of the target from the binding element leaving the binding element free for next target to bind, the complete process refers to a complete cycle. Depending on efficiency of the binding element, the number of cycles can be repeated. As the binding elements are coupled with a substrate, the substrate may also maintain the structural integrity for multiple uses.

The solid support may be a surface of any solid material or a substance. The non-limiting examples of solid support may include a glass slide, a sensor chip, a petri-plate, a petri-dish, a test tube, a beaker, a container, a solid matrix, a hydrogel, a membrane. A solid material with an exposed surface may be used as a solid support, for example, a metal sheet, a glass slide or a plastic plate. The solid support may be a component of a system, wherein a surface of the component may function as a solid support for holding the substrate coupled binding elements.

As noted, in the embodiments, wherein the binding element is immobilized on a solid support, the binding element-target complex is also immobilized on the solid support. In some embodiments, the substrate coupled binding element has sufficient affinity and selectivity for the target, such that the substrate coupled binding element select the appropriate molecule as a target and binds the target to form a binding element-target complex.

In one or more embodiments, the binding element-target complex is washed with a washing solution. As noted, the "washing solution" may refer to a solution that provides a washing condition which does not destabilize the binding element-target complex. The washing solution may be selected depending on the binding element or the target, and the stability of the binding element-target complex. The washing may be performed when the complex is bound to a solid support. The washing may remove un-bound or non-specifically bound molecules present in the sample, or any impurities present in the solution comprising the binding element-target complex. In one or more embodiments, the washing comprises repeated washing cycles. Repeated washings may ensure presence of only specifically bound target to the binding element. In these embodiments, washing solution is used for washing the complex attached to the solid support. The post-wash liquid may be removed to eliminate any un-bound target, non-specifically bound other molecules or any impurities.

As noted, in one or more embodiments, the method further comprises dissociating and eluting the target from the complex using an "elution solution". As noted, an 'elution solution' may refer to a solution that elutes the target from the binding element-target complex using various methods. In some embodiments, the elution is achieved by one or more of the methods selected from: re-constituting the substrate coupled binding element-target complex in a solution to dissociate the target, washing the complex with either a buffer with a high ionic strength or using mild conditions, inducing a conformational change to the binding element or binding element-target complex.

As noted, the elution of the target is achieved by re-constituting the substrate coupled binding element-target complex in a solution to dissociate the target, wherein one or more elution solutions may be used. In some embodiments, the elution solution may regenerate the binding element for next or subsequent binding event. As noted, in one or more embodiments, the method further comprises dissociating the binding element-target complex to form the substrate coupled binding element and the target under mild conditions using an elution solution.

As noted, the binding element-target complex may be dissociated under mild conditions, the term "mild condition" refers to herein as a condition which causes minimum structural change of the binding element so that it can release the target, however the condition ensures minimum or no structural or functional change to the target. In some embodiments, the mild conditions allow recovery of the target in an un-denatured form with minimal aggregation or unfolding. In some embodiments, the mild condition causes a conformational change to the binding element and retains the intact structure and function of the target.

As noted, in some embodiments, the mild condition causes a conformational change to the binding element; one or more solutions may be added to the binding elements to regenerate the actual structure of the binding element. These solutions are referred to herein, as a "regeneration solution". The 'regeneration solution' may be used for regenerating the binding element under mild conditions. In some embodiments, the regeneration solution regenerates the binding elements by recovering the actual structure and function. In some embodiments, the regeneration solution also functions as elution solution, as the solution also elutes the target. In these embodiments, the regeneration solution is used for washing the complex and elutes the target. In these embodiments, the solution regenerates the binding element during elution of target or after elution of the target. In some embodiments, the requirement of elution and regeneration is different and that depends on the selection of binding element or target. In these embodiments, the regeneration solution only recovers the structure or function of the binding element but not elute the target. In some embodiments, the regeneration solution which helps to regain the actual structure of the binding element after conformational change to the binding element, may include, but are not limited to, a buffer with a high ionic strength, a diluted base, a salt solution or deionized water, guanidinium hydrochloride, sodium hydroxide, sodium chloride, and mixtures of sodium hydroxide and sodium chloride.

In some embodiments, when the mild condition causes minimum structural change to the target, the change is a reversible conformational change. In these embodiments, the target regains its original structure after recovery. For example, in the case of a nucleic acid based binding element, the conditions are selected that favor conformational change to the nucleic acid binding element however, maintains the tertiary structure and function of the target. As noted, the mild conditions allow for reuse of the binding element. In these embodiments, the regeneration solution is used to regenerate the binding element for multiple uses. In case of binding element used for detection or sensor applications, easy removal of analyte target allows reuse of the sensor, preferably many times over with minimal loss of binding capacity or destruction of the binding element. In these embodiments, minimal loss of binding capacity may also be recovered using one or more of the regeneration solutions.

One or more examples of the mild condition may include, use of deionized water, weak bases, salts or chelators. The deionized water may un-shield the charge on the phosphate backbone of nucleic acids (such as DNA) and hindering secondary structure formation. In some examples, dilute base, such as 0.1-50 mM may also be used to reduce secondary structure of the nucleic acids. The use of NaCl with a concentration of 1M or greater may also be used for effectively reducing ionic interactions. In some examples, the structure of the binding element is stabilized by metal ions, wherein the binding element may be destabilized using a metal chelator. In one embodiment, a liquid with low ionic strength, such as deionized water, is used to dissociate the target molecule. A liquid with low ionic strength is desired as the liquid helps in efficient downstream purification or detection; for example buffer exchange.

In some embodiments, the target present in the sample may be concentrated by adding the sample to the binding element such that the target binds to the binding element, where the binding element is bound to the solid surface (which is also referred to as "binding element bound to the solid surface"), purifying the target from non-target molecules by using a washing solution and eluting from the binding element bound to the solid surface by water, low ionic strength solution or other mild conditions. In some embodiments, the target may bind to multiple binding elements, such as the target may bind to a first binding element, a second binding element, a third binding element, a fourth binding element, and so on. The second, third, fourth and other binding elements may be referred to as "downstream binding elements." The target may further be detected downstream of binding to the first binding element bound to the solid surface. Conditions for elution of the target from the first binding element may retain the binding ability of the target to the downstream binding element. The "downstream" is defined herein, as the second binding element positioned after the first binding element in accordance to the sample flow path. Binding of the same or different binding element bound to a solid surface detection device may be used for detection. In some embodiments, different sets of binding elements are used for detection which may increase the selectivity for the target. Further, water or low ionic strength elution conditions are used for eluting the target from the binding element following pre-concentration step.

The elution may cause structural change to the binding element to release the target. The elution method ensures a minimum or no structural or functional change to the target. In some embodiments, a conformational change is induced to the binding element to release the target, wherein the target retains the intact structure and function. In some embodiments, a minimum structural change may result in the target, wherein the change is a reversible conformational change. In these embodiments, the target regains its original structure after recovery and re-constitution. For example, a target, such as a protein has a minimum conformational change during recovery with water or a buffer with low ionic strength. The protein target regains its original structure and function, when the target is reconstituted in a buffer with desired ionic strength.

In one or more embodiments, the binding element is coupled to a substrate, wherein the substrate comprises a polymer, a protein, a peptide, a carbohydrate, a small molecule or combinations thereof. In some embodiments, the substrate comprises a stimuli-responsive polymer. The stimuli-responsive polymer may comprise a thermoresponsive polymer, a pH responsive polymer, a pressure responsive polymer, a humidity responsive polymer, an ionic strength responsive polymer, a light responsive polymer or combinations thereof. A nonlimiting example of a stimuli-responsive polymer is a hydrogel such as dextran.

In some examples, the substrate is a tag or a linker, which includes, but are not limited to, a streptavidin coated bead, a histidine tag, a glutathione S-transferase (GST) tag, a maltose binding protein (MBP) tag, a fusion comprising an antibody Fc region, a bifunctional reagent linker, or a linker comprising biotin. In one embodiment, the substrate comprises a polymer. In some embodiments, the substrate comprises a stimuli responsive polymer. For example, the substrate is a thermoresponsive polymer, a pH responsive polymer, a light responsive polymer or combinations thereof. In some embodiments, the substrate comprises dual responsive polymer, such as a thermoresponsive polymer, which is also responsive to pH.

In some examples, the substrate is a sensor surface. The sensor surface may include, but are not limited to, glass, quartz, polymer, gold, platinum, nanoparticle surface, nanotube surface, or nanorod surface. The sensor is employed to detect the binding events, elution events or combinations thereof and ensure reversible binding/release cycles.

In one embodiment, the method is employed for reversible detection of a target. In these embodiments, the method comprises immobilizing one or more binding elements on a sensor surface, followed by contacting a sample comprising the target to the binding elements on the sensor surface. The contact between binding elements and target ensures forming a binding element-target complex in a target binding event. The sensor may comprise a detector for detecting the target-binding event to generate a detection signal. The detector may provide the information about the concentration of the target in the sample. The target is eluted from the binding element-target complex in an elution event; and the sensor determines a number of the target-binding event, the elution event or combinations thereof as counted from the beginning of the usage of the sensor surface followed by applying a correction to the detection signal based on the number of the binding event, the elution event or combinations thereof during the reversible detection of the target to improve accuracy of quantitation of target concentration over at least 100 bind/release cycles.

In another embodiment, a method for reversible detection of a target and quantitation of a target concentration in a sample is provided. The method comprises immobilizing one or more binding elements on a sensor surface and contacting a sample comprising the target to the binding elements to form a binding element-target complex in a target binding event. The target binding event is followed by detection of the target-binding event with a detector to generate a detection signal in proportion to the concentration of the target in the sample and eluting the target from the binding element-target complex in an elution event. After eluting the target, a regeneration solution is further applied to complete the removal of the target bound to the binding element and to regenerate the binding element in a regeneration event, determining a number of the target binding event, the elution event, the regeneration event or combinations thereof as counted from the beginning of the usage of the sensor surface. After these, a correction is applied to the detection signal based on the number of the target binding event, the elution event, the regeneration event or combinations thereof during the reversible detection of the target to accurately quantify the target concentration over at least 100 bind/release cycles.

The target molecule may be an organic molecule, an inorganic molecule, a biological molecule, a synthetic molecule or combinations thereof. In one or more embodiments, the target molecule may be a protein, a post-translationally modified protein, a peptide, a carbohydrate, a drug, a carrier, a small molecule, an adapter, a virus, a cell or combinations thereof. The term "carrier" refers to a compound that may attach to one or more drug, protein, peptide, carbohydrate, lipid, genetic material or small molecule for targeted delivery and controlled release. The carrier may include a synthetic compound or a natural compound isolated from different sources. The carrier may be a nanoparticle. In one embodiment, the target molecule is a protein or peptide. For example, the target molecule is thrombin. The target molecules may be present in a solution, an extract or a formulation, which may be present in a sample at a concentration, ranged between 1 pM and 1 mM.

In one or more embodiments, the binding elements function as affinity ligands and are selected for high affinity binding to molecular targets, wherein the oligomers are selected for synthesizing binding elements. In some embodiments, the binding element is an oligonucleotide sequence, a DNA sequence, an RNA sequence, a PNA sequence, a peptide sequence or combinations thereof. The binding element may comprise a protein binding sequence or one or more tandem repeat sequences or one or more protein binding sequences. In some embodiments, the binding elements are ranging between 15-60 nucleotides in length. The binding element may include substitutions on the base portion of DNA to enhance hydrophobic interactions with target molecules. In an exemplary embodiment, the binding element comprises a DNA aptamer, which is attractive for its pH and thermal stability, small size (~13 kDa), and high binding efficiency. DNA aptamers may be considered as an efficient affinity binder in the context of downstream processing. The ease of binding element synthesis may be an additional benefit, since it allows synthesizing a less expensive binding element compared to its protein-based counterparts, in addition to reproducibility in synthesis process. A further favorable characteristic of DNA binding element is easy manipulation that disrupts the secondary structure of the binding element which leads to dissociation of the target from the binding element, enabling recovery of the target molecule using mild elution conditions.

FIG. 1 is a flow chart illustrating an exemplary embodiment of a method 30 for selecting a specific target 34 using binding element 32 immobilized on a solid support. In an alternative embodiment, some of the steps may be performed simultaneously or in different order. In some embodiments, one or more steps may be added to the flow chart. Nonlimiting examples of these steps include detecting the concentration of the target bound to the binding element immobilized on a solid support and counting the number of the target binding events, the number of elution events as counted from the beginning of the usage of the solid support. The flow chart of FIG. 1 includes the step of adding a sample comprising a target 34 to the binding element 32 to form a binding element-target complex 36. The binding element-target complex 36 is washed to recover purified binding element-target complex 40, wherein the impurities 38 are removed. The washing is followed by elution of the target 42 from the binding element 32 immobilized on a solid support. In one or more embodiments, the solid support immobilized binding element is couples to a substrate or a linker. In one or more embodiments of the method, the binding element 32 immobilized on a solid support is recycled for repeated use.

Figure 2:
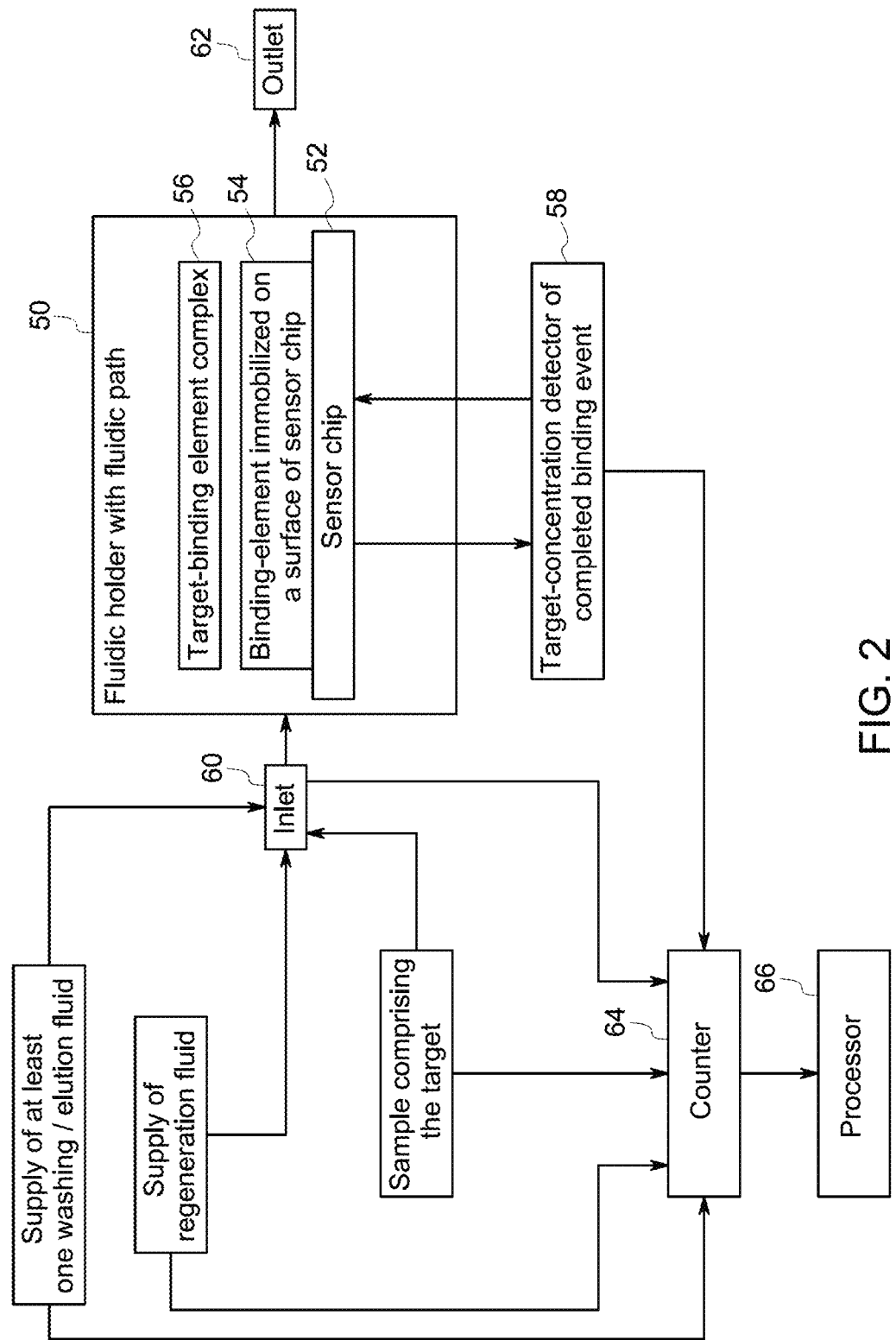
FIG. 2 is a schematic diagram showing a system for target detection using binding elements in accordance with one embodiment of the invention.

An embodiment of a system for reversible detection of a target is provided herein in FIG. 2, wherein the system comprises a sample holder 50 with a fluidic path comprising a sensor chip 52 with one or more binding elements immobilized on a surface of the sensor chip 54. If a sample comprising a target is added to the surface of the sensor chip 54, a target-binding element complex formed and bound to the sensor chip 56. The system further comprises a target concentration detector 58 to detect the sensor signal level upon target binding events. The system further comprises one or more inlets 60 to supply at least one washing or elution solution and samples comprising an unknown concentration of the target.

During operation, a sample comprising the unknown concentration of the target is applied to the sensor via system inlet 60. A washing solution and an eluting solution are also supplied through the system inlet 60 for washing or elution, respectively. After applying the washing or elution solution, a regeneration solution is applied to regenerate the binding element. The system further comprises an outlet 62 for removing post wash liquid. The system also comprises a counter 64 and a processor 66. The system allows binding of the target to the surface-immobilized binding elements followed by release of the specifically bound target, wherein the binding/release cycle may be repeated for multiple times. The lines with arrows in FIG. 2 connecting the individual components illustrate the electrical or fluidic relations between the different components of the system.

In another embodiment, the system comprises at least two sensing regions with immobilized binding elements, where each region contains a different type of the immobilized binding elements. The sample with unknown concentration of the target is sequentially or in parallel introduced to each of the sensing regions. The sequential or parallel operation with at least two sensing regions provides the improved selectivity of determination of target binding.

The surface is configured to load a sample comprising the target to complete a binding event forming a binding element-target complex. As noted, the term "configured to" refers to structure or configuration of the surface, wherein one or more binding elements are attached to the surface. The term "immobilized" refers to herein as the binding elements are attached to the surface, such that the binding elements are tightly bound to the surface. The binding elements may have minimum possibility to detach from the surface during system operation. The attachment of the binding elements to the surface is achieved by using known techniques with nonlimiting examples that include a covalent attachment using thiol, amine, or hydroxysuccinimidyl functionalization and an attachment using streptavidin-biotin immobilization chemistry. In some embodiments, the binding elements are immobilized on the surface through one or more substrates. The substrate may include a polymer, a metal, a cellulose, a glass, a peptide, a carbohydrate or combinations thereof.

The embodiments of the system further comprise an inlet 60 to supply a first solution to wash the binding element-target complex. As noted, the system also comprises another inlet to supply a second solution to elute the target from the binding element-target complex to complete an elution event. In some embodiments, the system comprises a single inlet 60 that supplies both the first solution and the second solution, depending on requirement. In these embodiments, the system comprises a valve near the inlet, and the inlet may be connected to two different reservoirs, one contains first solution and the other contains second solution. The system also comprises an inlet that supplies a regeneration solution (or regeneration solution) that is applied to regenerate the binding element. A regeneration solution changes the conformation of the binding element that allows releasing the bound target.

The system may also comprise a controller, that controls the valve and release the required solution to the system during the binding or release cycle. The system may further comprise one or more chambers configured to hold one or more solutions, such as a first solution or a second solution. The system may further comprise a collection chamber for collecting the target after elution. As noted, one or more solutions may be used, for example when the process requires washing under different conditions to achieve a fast washing or second washing. The system may further comprise additional chambers configured to hold additional solutions. The system may further comprise specific environmental controllers, such as a heating element or a UV light source.

As noted, the system further comprises a target-concentration detector 58, wherein the detector 58 detects complete binding event. A target-concentration detector 58 measures the concentration of the target that may be bound to the immobilized binding element. Nonlimiting examples of such a target-concentration detector include optical detector, electronic detector, electrochemical detector, gravimetric detector, mechanical detector, plasmonic detector, impedance detector, acoustic-wave detector, or any other detector known in the art.

As noted, the system further comprises a counter 64 for detecting, counting and logging the number of the binding events, the elution event or combinations thereof as counted from the beginning of the usage of the sensor surface for reversible operation of the binding element. A nonlimiting example of such a counter 64 is an electronic circuit that counts events of operating the target-concentration detector and performing washing steps.

In one or more embodiments, a washing event and an elution event are different. A washing event is wash with a buffer that maintains binding of target to the binding element, wherein the wash buffer may be similar buffer that used to select the binding element. Washing is included to remove non-targets that are either physically entrapped or non-specifically bound non-targets. In these embodiments, the solutions are used to dissociate the target from the binding element. The solutions generally used for elution may be different from the solutions used to select the binding element for the target, such as, water, solution with low ionic strength, solution of dilute base (0.1-50 mM), or solution comprising chelators, chaotrope or salt used for washing solution.

The embodiments of the system also comprise a processor 66 for calibrating performance of the system for reversible operation of the immobilized binding elements. The processor 66 may provide a dissociation constant of the binding elements immobilized on the surface after each elution event. The processor 66 may further analyze a sensor response value for further correction. The processor may also store the sensor calibrations based on the tested target concentrations and the number of bind/release cycles for the sensor. In some embodiments, the system comprises a counter 64 which is synchronized with the processor 66 and compensates any loss of binding capacity. In some embodiments, the counter 64 together with the processor 66 allows for compensation of any loss of binding capacity of the sensor chip with the immobilized binding element and preserves the accuracy of the determinations of the bound target upon multiple operation cycles of the sensor. The compensation of the loss of binding capacity of the sensor chip with the immobilized binding element may be performed by the prior determination of the loss of binding capacity of the sensor chip with the immobilized binding element during the calibration routines, determination of the mathematical functional relationship between the loss of binding capacity of the sensor chip with the immobilized binding element and the number of the operation cycle and storing the mathematical functional relationship in the memory of the processor.

Figure 3:
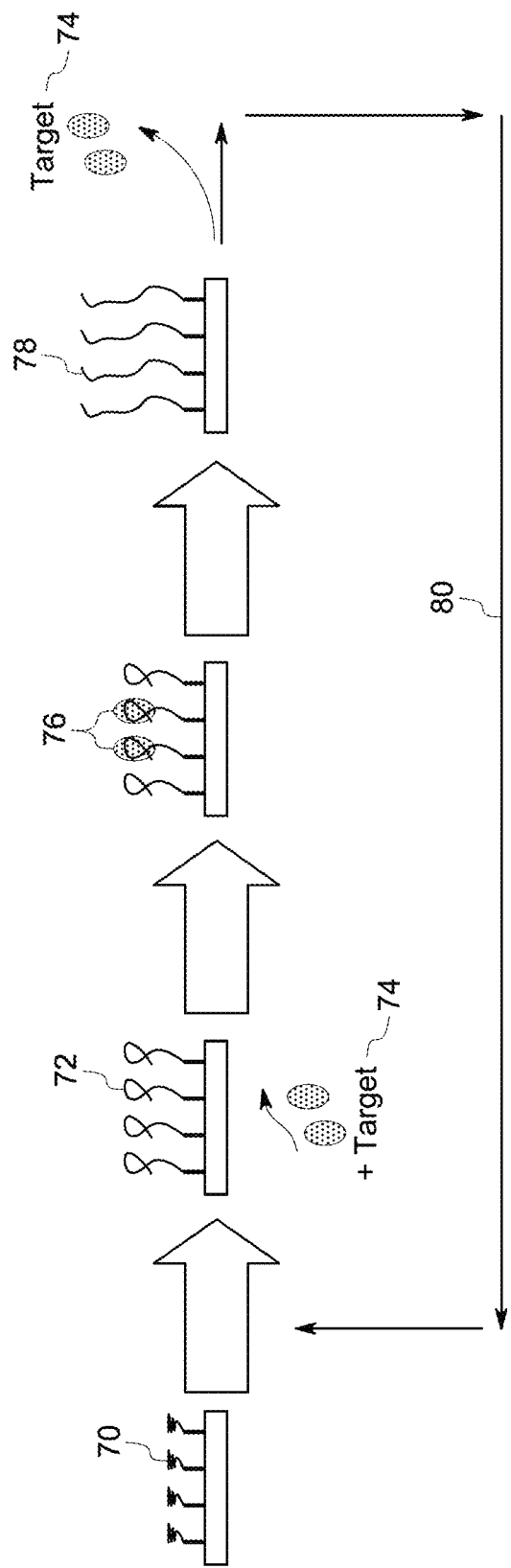
FIG. 3 is a schematic representation of a process flow diagram using the system, wherein the system performs multiple cycles of the detection in accordance with one embodiment of the invention.

FIG. 3 shows an exemplary embodiment of a process flow diagram using the system, wherein the system performs multiple cycles of the detection. In one embodiment, a system for reversible detection of a target comprises a sample holder comprising one or more binding elements immobilized on a surface 70, as shown in FIG. 3. In some embodiments, the binding elements are activated using a buffer or water, forming activated binding elements 72. The surface is configured to load a sample comprising the target 74 to complete a binding event. The binding event results in forming a binding element-target complex 76. The system further comprises an inlet to supply at least a first solution to wash the binding element-target complex and an inlet to supply at least a second solution to elute the target from the binding element-target complex to complete an elution event. Using one or more solution, the binding elements are deactivated, 78. The deactivated binding elements release the target 74. The system may further comprise a target-concentration detector 58 to measure the concentration of the target that may be bound to the immobilized binding element. A counter may be present in the system for counting the binding event, elution events or combinations thereof as counted from the beginning of the usage of the surface. The system may further comprise a processor for calibrating 80 performance of the system based on the number of prior performed bind/release cycles for an accurate reversible operation of the immobilized binding elements (FIG. 3).

In some embodiments, upon reversible operation of the sensor comprising binding elements immobilized on the sensor surface, the sensor surface experience degradation. A non-limiting example of the term "degradation" refers to a spontaneous detachment of the immobilized binding elements from the surface. The degradation causes a reduced sensor response pattern upon detecting the target. In some embodiments, the degradation is proportional to the total number of bind/release cycles performed on the sensor surface. In these embodiments, the degradation is substantially independent of the concentration of the target in the samples. Thus, by knowing the number of performed bind/release cycles, the detector response may be corrected with regard to the degradation of sensor surface. This correction improves the accuracy of detection.

As noted, in some embodiments, the system comprises a target-concentration detector to detect a concentration of the target molecules. The accuracy for determination of the target concentration in a sample may be improved. In some embodiments, the accuracy may be improved by counting the number of events, such as binding events, washing events, elution events and regeneration events as counted from the beginning of the usage of the sensor surface, followed by comparing the number of the events to the degradation events of the sensor. As noted, "accuracy", refers to herein as proximity of concentration of the target in a sample measured by the system compared to the actual concentration measured by a reference instrument or as prepared by the dilution of a known concentration.

A number of binding event, elution event, or combinations of both for the reversible operation may be in a range from 2 to 1,000 times. In some embodiments, a number of binding event, elution event, or both of the reversible operations are in a range from 2 to 1,000,000.

Example 1. Reversible Operation of Biosensor with Immobilized Binding Elements for 365 Cycles Using 50 mM NaOH/1 M NaCl Solution for Sensor Regeneration A thrombin specific binding element sequence GGTTGGTGTGGTTGG (SEQ. ID. NO. 1) and a control binding element sequence GGTGGTGGTTGTGGT (SEQ. ID. NO. 2) were extended with 20 polyT nucleotides and were used for the experiments. Binding elements were additionally functionalized with biotin at their 5' end. The thrombin specific binding element was immobilized on streptavidin-functionalized (SA) chips (BR-1000-32, GE Healthcare). Chips were first conditioned with three consecutive injections of 1 M NaCl/50 mM NaOH for 1 min. The thrombin specific binding elements were immobilized on the SA chip by loading the binding element solution individually through each channel at a flow rate of 10 μl/min for 1 minute followed by washing the chip with a HEPES buffer (0.01 M HEPES pH 7.4, 0.15 M NaCl, 3 mM EDTA and 0.005% (v/v) Surfactant P20) for 7.5 minutes. The control binding element comprises oligonucleotide comprised of a randomized sequence of similar length and nucleic acid base content and was applied at a similar loading density as the binding element to the reference channel to compensate for non-specific binding.

Figure 4:
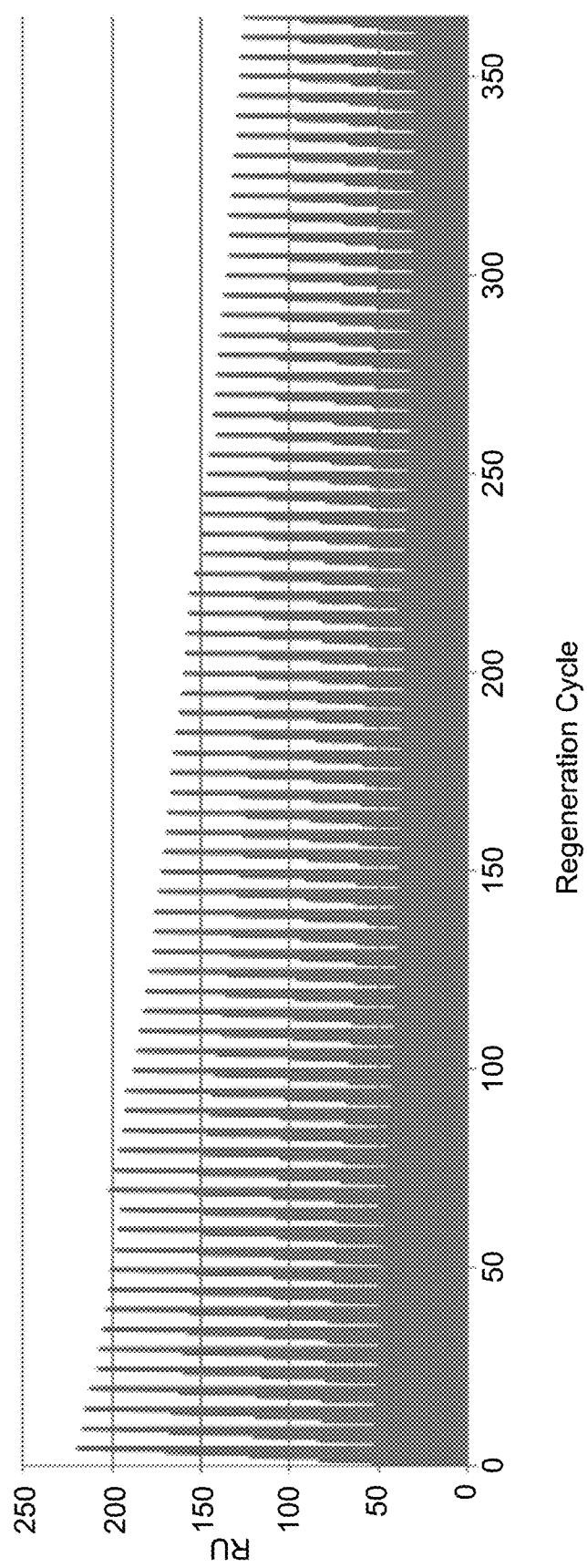
FIG. 4 is a graph showing binding of thrombin followed by regeneration of the thrombin specific binding element in accordance with one embodiment of the invention.

The binding capability of the thrombin specific binding elements upon 365 binding/release cycles were carried out with thrombin concentrations of 0.5, 1, 2, 4, and 8 nM, as shown in FIG. 4. The flow rate was set at 20 μl/min. The thrombin binding buffer contained 0.01 M HEPES pH 7.4, 0.15 M NaCl, 3 mM EDTA and 0.005% (v/v) Surfactant P20 (BR-1001-88, GE Healthcare) containing 5 mM $MgCl_2$ (running buffer). The regeneration (injection time 0.5 min) after each cycle was carried out with a mixture of 50 mM NaOH/1 M NaCl.

Figure 5:
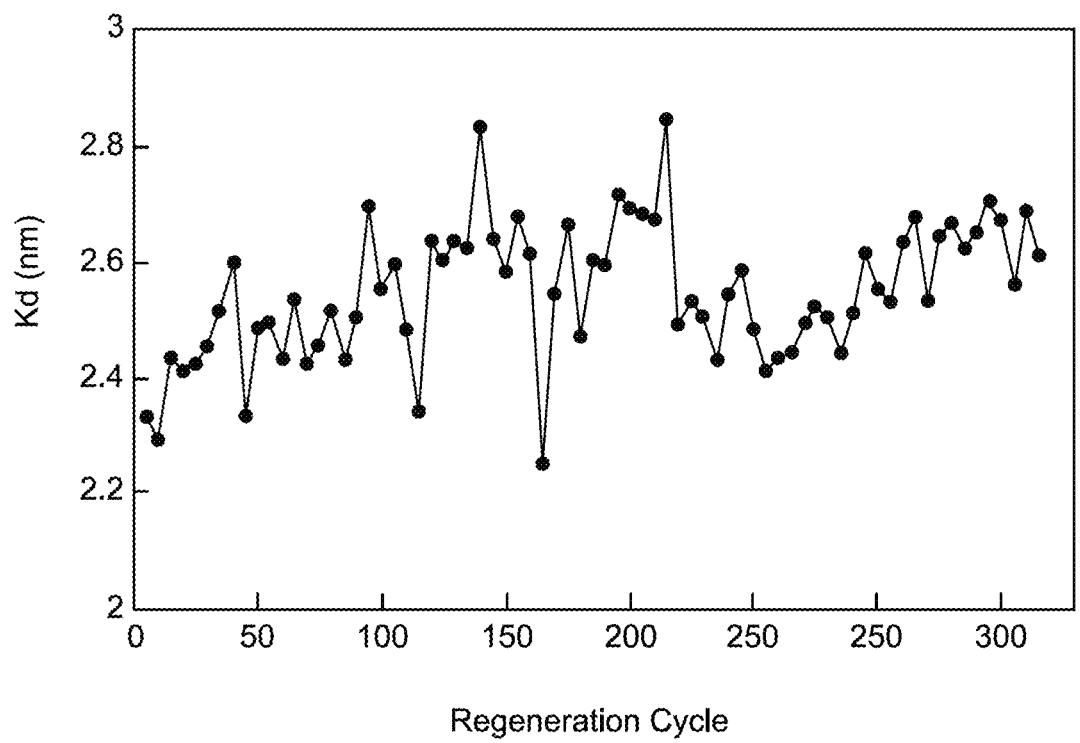
FIG. 5 is a graph showing high stability of the binding constant $K_d$ for Thrombin during 365 bind/release cycles of reversible operation as a function of performed bind/release cycles.
Figure 6:
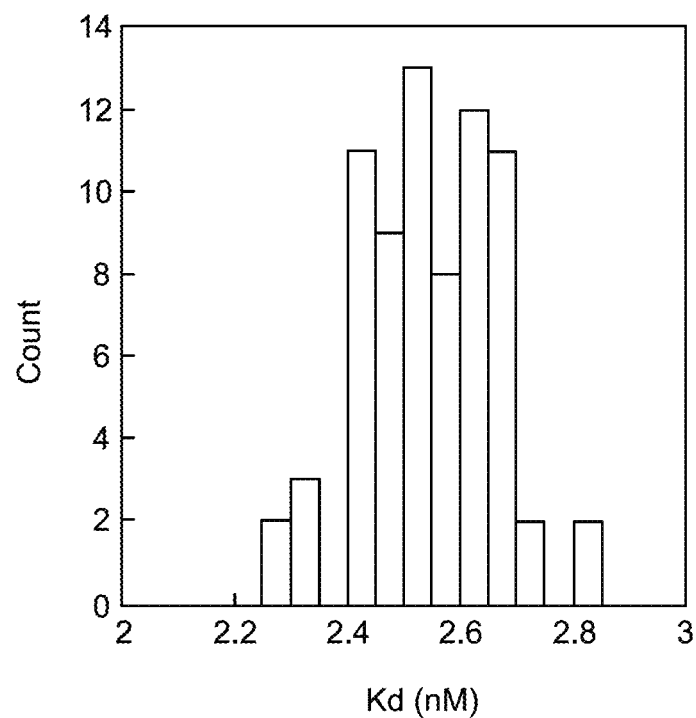
FIG. 6 is a histogram showing the binding constant $K_d$ for thrombin during 365 bind/release cycles.

The data obtained in FIG. 4 was further processed to estimate the binding affinity $K_d$ of the binding element for thrombin. A global fit of binding interactions at five concentrations of thrombin provided a $K_d$ of ~2.5±0.1 nM, consistent with literature values of 1-10 nM based on different immobilization conditions and detection methods. FIG. 5 depicts $K_d$ values with the number of the bind/release cycle of reversible performance of the immobilized binding element. FIG. 6 shows the $K_d$ is consistent throughout the 365 cycles of regeneration. Immobilized binding element demonstrates in FIGS. 5 and 6, high stability of the binding constant $K_d$ during their 365 bind/release cycles of reversible operation. FIG. 5 illustrates the binding constant $K_d$ as a function of performed bind/release cycles for thrombin, wherein FIG. 6 shows histogram of the binding constant $K_d$ over 365 bind/release cycles, $K_d$=2.5±0.1 nM (mean±1σ).

Figure 7:
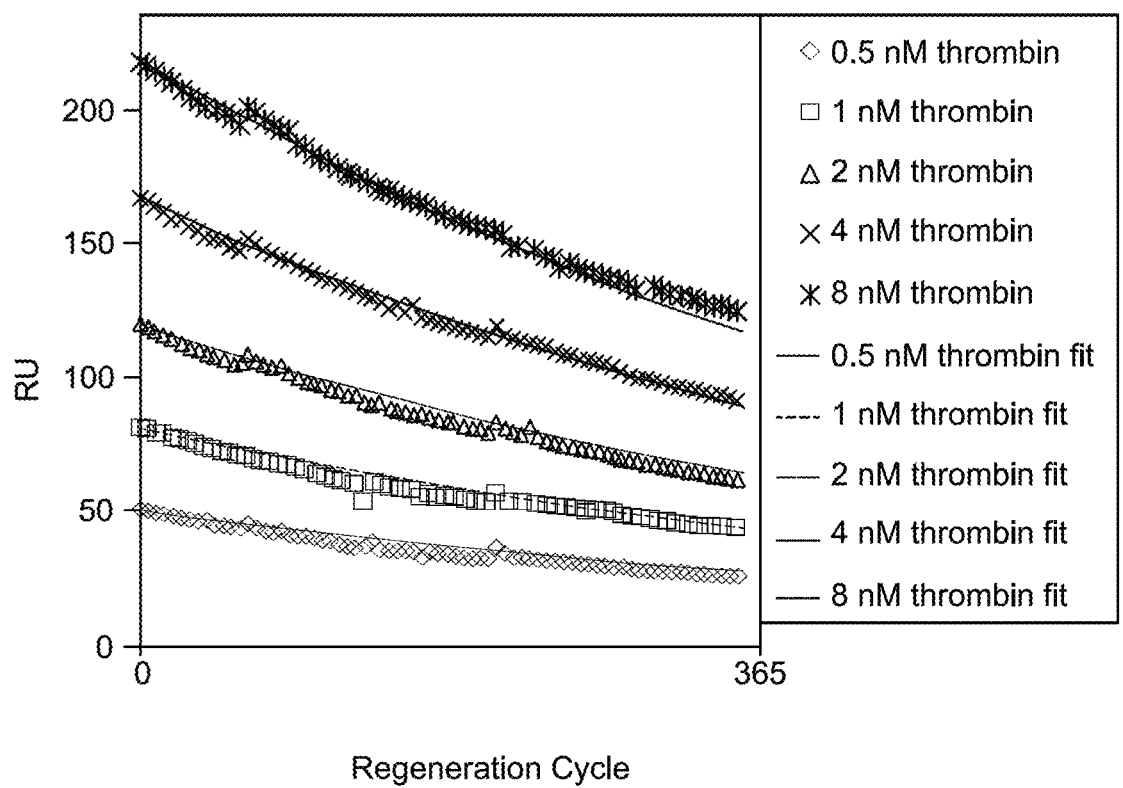
FIG. 7 is a series of graphs showing detection of thrombin using varying concentrations over 365 bind/release cycles for reversible operation using immobilized thrombin specific binding element.
Figure 8:
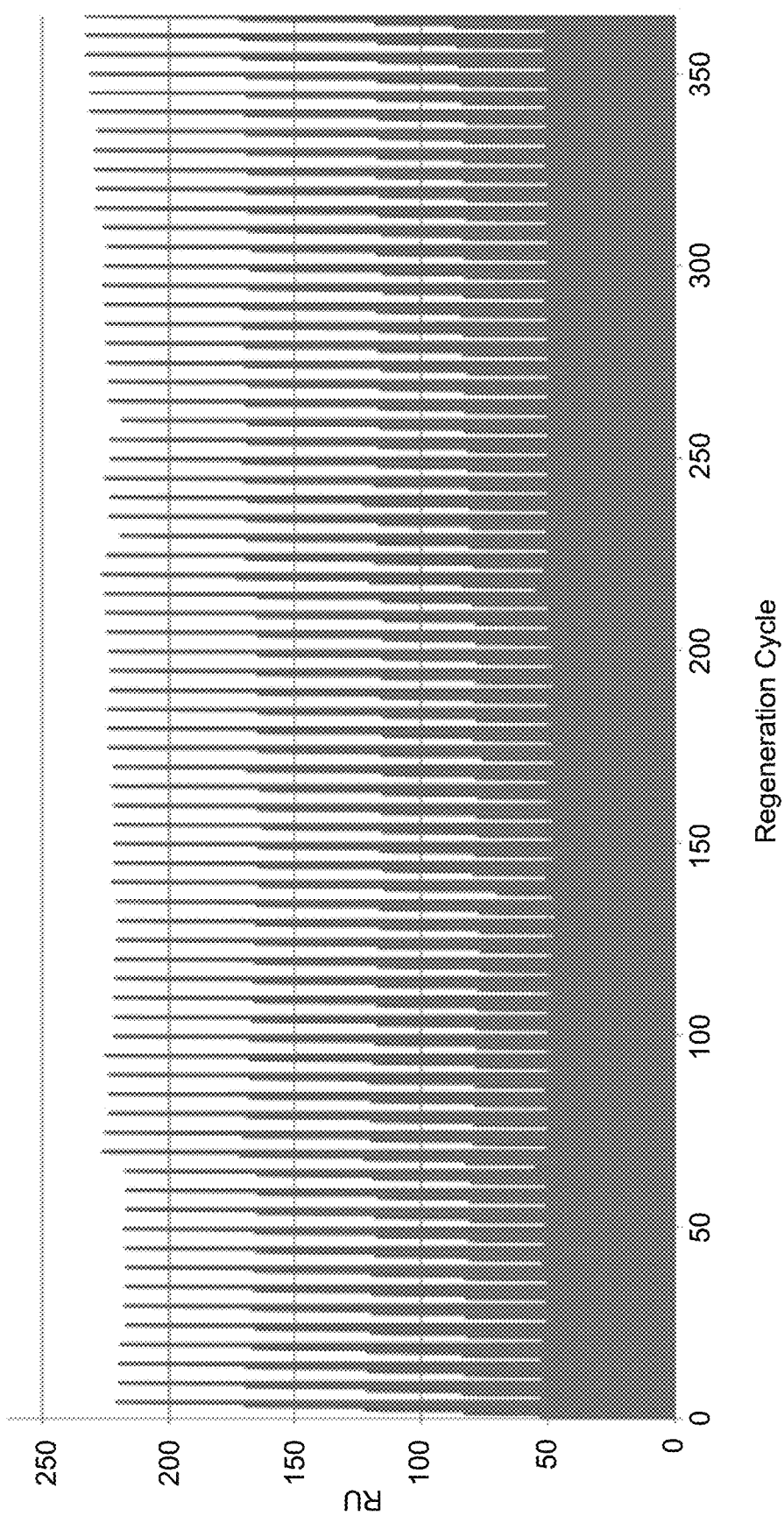
FIG. 8 is a graph showing detection of thrombin using corrected sensor response.

The gradual loss of binding signal in FIG. 4 was likely due to the slow but not insignificant dissociation rate of biotin-streptavidin of the biotinylated binding element from the streptavidin surface. The reduction in binding capacity of the aptamer-functionalized streptavidin chip was analyzed from the standpoint of the streptavidin-biotin linker chemistry. While the streptavidin-biotin interaction is uncommonly strong with $K_d$~$10^{-14}$M, its finite dissociation rate was noticeable over experiments with 365 cycles (FIG. 4). The results of a global fit to the change in maximal signal prior to the thrombin dissociation phase for the five thrombin concentrations used in our studies are presented in FIG. 7. This global fit estimated a dissociation rate for biotin from the streptavidin to be $(1.6±0.1)×10^{-6}$ s$^{-1}$. The experimentally determined $1.6×10^{-6}$ s$^{-1}$ correction factor was further applied to the original plasmon resonance signal shown in FIG. 4. This correction (FIG. 8) successfully normalized the signal for the duration of the 365 regeneration cycles. Covalent attachment of aptamers to detection surfaces or the thermo-precipitable polymer improves the reusability of the aptamer. FIG. 8 illustrates accurate detection of thrombin after sensor signal correction over 365 bind/release cycles of reversible operation of immobilized thrombin aptamer bioreceptors.

Example 2. Reversible Operation of Biosensor with Immobilized Binding Elements for 100 Cycles Using Deionized Water for Sensor Regeneration A thrombin specific binding element sequence and a control binding element sequence were same as in Example 1, also extended with 20 polyT nucleotides and additionally functionalized with biotin at their 5' end. The thrombin specific binding element was immobilized on streptavidin-functionalized (SA) chips (BR-1000-32, GE Healthcare) same as in Example 1.

Figure 9:
FIG. 9 is a graph showing binding of thrombin followed by regeneration of the thrombin specific binding element using deionized water in accordance with one embodiment of the invention.

A study of 100 cycles of regeneration was conducted using deionized water as regeneration solution. The injection time of 15 min was used for water regeneration Thrombin concentrations were 1 nM, 2.5 nM, 5 nM, 10 nM and 20 nM. The 20 cycles were performed for each of injections. Before each thrombin binding experiment, at each concentration, the bound binding element was regenerated with deionized water. FIG. 9 shows results of binding of thrombin followed by regeneration of the thrombin specific binding element with deionized water.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for reversible detection of a target using a target detection system, comprising:
   immobilizing one or more binding elements on a sensor surface;
   contacting a sample comprising an unknown concentration of the target to the binding elements on the sensor surface to form a binding element-target complex in a target-binding event, the target and binding element having a consistent binding affinity over at least 100 bind/release cycles, wherein the consistent binding affinity (Kd) is within ±0.1 nM standard deviation;
   detecting the target-binding event with a detector to generate a detection signal;
   eluting the target from the binding element-target complex in an elution event;
   applying a regeneration solution to complete removal of the target from the binding element-target complex in a regeneration event;
   determining a number of the target-binding event, the elution event, regeneration event or combinations thereof using a counter of the target detection system, the number representing a count of the target-binding event, the elution event, regeneration event or combinations thereof since the beginning of usage of the sensor surface; and
   applying a correction to the detection signal based on a global fit calculated for each of the number of the target-binding event, the elution event, the regeneration event or combinations thereof during the reversible detection of the target over at least 100 bind/release cycles.

2. The method of claim 1, wherein the correction to the detection signal improves detection accuracy of a concentration of the target in the sample.

3. The method of claim 1, wherein a number of the reversible detection is in a range from 100 to 1,000,000.

4. The method of claim 1, wherein a number of the reversible detection comprising binding event, elution event, or combinations thereof is in a range from 100 to 1,000.

5. The method of claim 1, wherein the elution is achieved by washing the sensor with a dilute base, a salt solution, a buffer, a chelator or combinations thereof.

6. The method of claim 1, where the global fit is based on the change in maximal signal for each cycle at different concentrations.

7. A method for reversible detection of a target and quantitation of a target concentration in a sample using a target detection system, comprising:
   immobilizing one or more binding elements on a sensor surface, contacting a sample comprising the target to the binding elements to form a binding element-target complex in a target-binding event, the target and binding element having a consistent binding affinity over at least 100 bind/release cycles, wherein the consistent binding affinity (Kd) is within ±0.1 nM standard deviation;
   detecting the target-binding event with a detector to generate a detection signal; eluting the target from the binding element-target complex in an elution event;
   applying a regeneration solution to regenerate the binding element in a regeneration event; determining a number of the target binding event, the elution event, the regeneration event or combinations thereof using a counter of the target detection system, the number representing a count of the target-binding event, the elution event, regeneration event or combinations thereof since the beginning of usage of the sensor surface; and applying a correction to the detection signal based on a global fit calculated for each of the number of the target binding event, the elution event, the regeneration event or combinations thereof during the reversible detection of the target and quantitation of the target concentration over at least 100 bind/release cycles.

8. The method of claim 7, wherein the correction to the detection signal improves detection accuracy of a concentration of the target in the sample.

9. The method of claim 7, wherein a number of the reversible detection is in a range from 100 to 1,000,000.

10. The method of claim 7, wherein a number of the reversible detection comprising binding event, elution event, or combinations thereof is in a range from 100 to 1,000.

11. The method of claim 7, wherein the elution is achieved by washing the sensor with a dilute base, a salt solution, a buffer, a chelator or combinations thereof.

12. The method of claim 7, where the global fit is based on the change in maximal signal for each cycle at different concentrations.

* * * * *